(12) United States Patent
Mark

(10) Patent No.: US 10,342,564 B2
(45) Date of Patent: Jul. 9, 2019

(54) VARIABLE ASPIRATION CONTROL DEVICE

(71) Applicant: Nico Corporation, Indianapolis, IN (US)

(72) Inventor: Joseph L. Mark, Indianapolis, IN (US)

(73) Assignee: Nico Corporation, Indianapolis, IN (US)

( * ) Notice: Subject to any disclaimer, the term of this patent is extended or adjusted under 35 U.S.C. 154(b) by 928 days.

(21) Appl. No.: 14/669,535

(22) Filed: Mar. 26, 2015

(65) Prior Publication Data

US 2015/0196315 A1    Jul. 16, 2015

Related U.S. Application Data

(63) Continuation-in-part of application No. 13/628,972, filed on Sep. 27, 2012, now Pat. No. 9,445,831.

(51) Int. Cl.
*A61M 1/00* (2006.01)
*A61B 17/32* (2006.01)
*A61B 17/00* (2006.01)

(52) U.S. Cl.
CPC ..... *A61B 17/32002* (2013.01); *A61M 1/0047* (2013.01); *A61B 2017/00017* (2013.01); *A61B 2017/00261* (2013.01); *A61B 2017/00738* (2013.01); *A61B 2017/00977* (2013.01); *A61B 2017/320028* (2013.01); *A61B 2217/005* (2013.01)

(58) Field of Classification Search
CPC ....................... A61M 1/0047; A61B 17/32002
See application file for complete search history.

(56) References Cited

U.S. PATENT DOCUMENTS 2,863,287 A    12/1958  Berkman
3,395,705 A     8/1968  Hamilton
(Continued)

FOREIGN PATENT DOCUMENTS

WO        9309839 A1    5/1993
WO     2010096139 A2    8/2010

OTHER PUBLICATIONS

PCT International Search Report and Written Opinion dated Jan. 2, 2014 for PCT/US2013/061667.
(Continued)

*Primary Examiner* — Ariana Zimbouski
(74) *Attorney, Agent, or Firm* — Kristin L. Murphy; Honigman LLP

(57) ABSTRACT

An aspiration control device may include a conduit having a distal end and a proximal end. The conduit may define a conduit lumen and an aperture vent open to the conduit lumen. A coupling may be configured to couple the proximal end of the conduit with a vacuum source and an inner cannula of a tissue cutting device. The inner cannula may define an inner cannula lumen wherein the vacuum source is configured to supply a vacuum to each of the coupling lumen and the inner cannula lumen. A sleeve may be movably disposed about the conduit, and a device motor may be in communication with the sleeve and be configured to move the sleeve to a predefined position relative to the vent in response to an input single from a user interface. The predefined position of the sleeve may correspond to a predefined level of vacuum to be supplied to the inner cannula lumen.

11 Claims, 11 Drawing Sheets

(56) References Cited

U.S. PATENT DOCUMENTS

| | | | |
|---|---|---|---|
| 4,764,165 A | | 8/1988 | Reimels et al. |
| 5,134,996 A | | 8/1992 | Bell |
| 5,195,961 A | | 3/1993 | Takahashi et al. |
| 5,429,601 A | | 7/1995 | Conley et al. |
| 5,505,210 A | * | 4/1996 | Clement ................ A61B 10/04 600/566 |
| 5,797,907 A | * | 8/1998 | Clement ................ A61B 10/04 606/45 |
| 5,899,884 A | | 5/1999 | Cover et al. |
| 6,258,111 B1 | | 7/2001 | Ross et al. |
| 6,290,690 B1 | | 9/2001 | Huculak et al. |
| 6,425,883 B1 | | 7/2002 | Urich et al. |
| 7,537,594 B2 | | 5/2009 | Sartor |
| 2009/0005747 A1 | * | 1/2009 | Michaels ............ A61M 1/0001 604/319 |
| 2009/0124975 A1 | | 5/2009 | Oliver et al. |
| 2009/0157002 A1 | | 6/2009 | Dumot et al. |
| 2009/0228030 A1 | | 9/2009 | Shadeck |
| 2010/0152756 A1 | * | 6/2010 | Mark ................ A61B 10/0275 606/167 |
| 2013/0035634 A1 | * | 2/2013 | Cappello ................ A61M 5/30 604/68 |

OTHER PUBLICATIONS

Catalog for Cusa Nxt, Ultrasonic Tissue Alation Systaem, "Touch the Next Wave", Integra Neuro Sciences.
Ultrasonic Catalog for Cusa Nxt/Selector, Integra Neuro Sciences.

\* cited by examiner

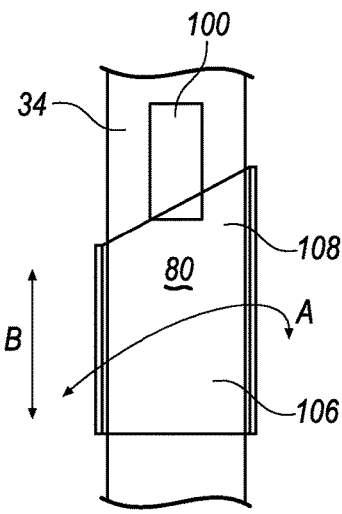
FIG. 6
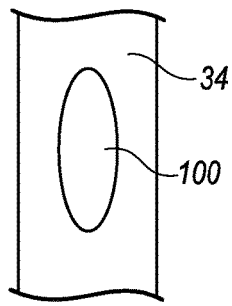 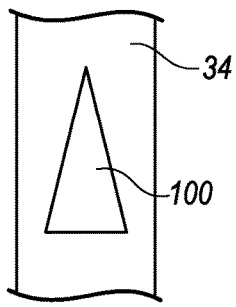 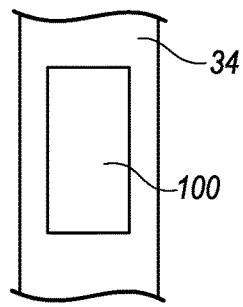 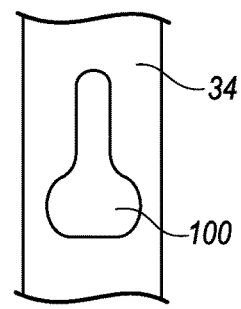
FIG. 7A        FIG. 7B        FIG. 7C        FIG. 7D
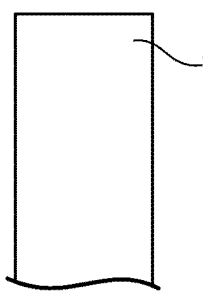 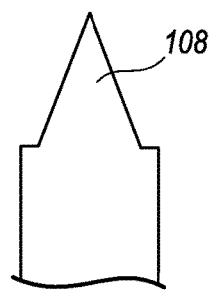 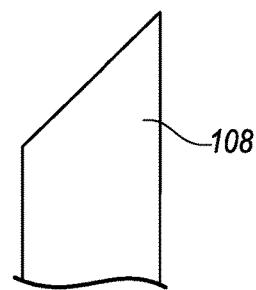
FIG. 8A        FIG. 8B        FIG. 8C de of FIG. 1.

VARIABLE ASPIRATION CONTROL DEVICE

CROSS-REFERENCE TO RELATED APPLICATIONS

This application is a continuation-in-part of U.S. application Ser. No. 13/628,972 filed Sep. 27, 2012, now published as U.S. 2014/0088526, the disclosure of which is hereby incorporated in its entirety by reference herein.

TECHNICAL FIELD

The present disclosure relates to surgical devices, in particular, surgical devices that perform multiple functions and that are suited for neurosurgical and spinal surgical procedures.

BACKGROUND

Various abnormalities of the neurological system, such as brain and spinal tumors, cysts, lesions, or neural hematomas, can cause severe health risks to patients afflicted by them, including deterioration in motor skills, nausea or vomiting, memory or communication problems, behavioral changes, headaches, or seizures. In certain cases, resection of abnormal tissue masses is required. However, given the complexity and importance of the neurological system, such neurosurgical procedures are extremely delicate and must be executed with great precision and care.

Traditional tissue removal systems such as suction cannula, shavers and ultrasonic aspiration system have a predefined level of aspiration or vacuum delivered to the tip of the device. This predefined level of vacuum is usually defined by a vacuum source and may be either completely turned on or completely turned off. Some systems attempt to supply levels of vacuum somewhere in between the on and off configuration by creating a bleed hole for the vacuum supply that allows a portion of the vacuum to be bleed out of the inner cannula, thus reducing the level of vacuum supplied to the tip. A user may elect to cover a portion of the bleed hole by using the user's fingertip to cover all or a portion of the hole. By allowing the hole to be covered, only a portion of the vacuum supply is bleed through the hole, thus creating a level of vacuum less than the vacuum supplied by the vacuum source. However, this technique does not allow for a variable, reproducible level of vacuum.

Other tissue removal systems employ peristaltic systems. In peristaltic systems, a pump is set to a specific speed to generate vacuum. However, hysteresis that peristaltic systems exhibit provide difficulties to achieve instantaneous flow changes. For example, peristaltic pumps lack the ability to immediately vent vacuum pressure from a peristaltic pump system to atmosphere. Accordingly, when it becomes desirable to release tissue from a surgical device, for example when the instrument comes into contact with a critical structure, the operation of the peristaltic pump is not capable of immediately responding to a vent input. Instead, the operator is required to wait until the pump can adjust and necessary equilibrium of the system is restored. Such actions may result in surgeon fatigue during a surgical action, as well as potential damage to tissue where it is necessary to immediately release tissue.

Peristaltic pumps often also exhibit a pulsed flow, particularly at low rotational speeds of the peristaltic pump. Thus, peristaltic pumps are less suitable where a smooth consistent flow is required.

BRIEF DESCRIPTION OF THE DRAWINGS

FIG. 6 is a partial top plan view of a portion of the aspiration control device of FIG. 5.

FIGS. 7A-D are partial top plan views of a portion of exemplary configurations of the conduit of the aspiration control device of FIG. 6.

FIGS. 8A-C are partial top plan views of a portion of exemplary configurations of the sleeve of the aspiration control device of FIG. 6.

DETAILED DESCRIPTION

Described herein is a tissue cutting device that is suited for neurosurgical applications such as the removal of spine and brain tissue. The cutting device is configured to connect to an existing vacuum supply, which may include a vacuum system hose fluidly connected to an existing vacuum source in a wall of a surgical room. The vacuum supply may supply a predefined level of vacuum to a tip of an inner cannula lumen of the cutting device. The tissue cutting device may be configured to include an aspiration control device configured to control the level of vacuum supplied to the tip. The control device may have a conduit defining an aperture vent and a sleeve encompassing the conduit. The sleeve may be configured to move with respect to the conduit in order to expose various portions of the vent. The level of vacuum applied to an inner cannula lumen may be controlled by a handpiece or a foot pedal by exposing various portions of the vent. Accordingly, the aspiration control device may control the level of vacuum in a steady, fixed and repeatable manner.

While described herein in the context of a tissue cutting device, it understood that the principles of the disclosure may be employed with a variety of other surgical devices. Examples of such surgical devices include, but are not limited to, rotary shavers, reciprocating cutting devices, ultrasonic aspirators, and ablative technology instruments.

Figure 1:
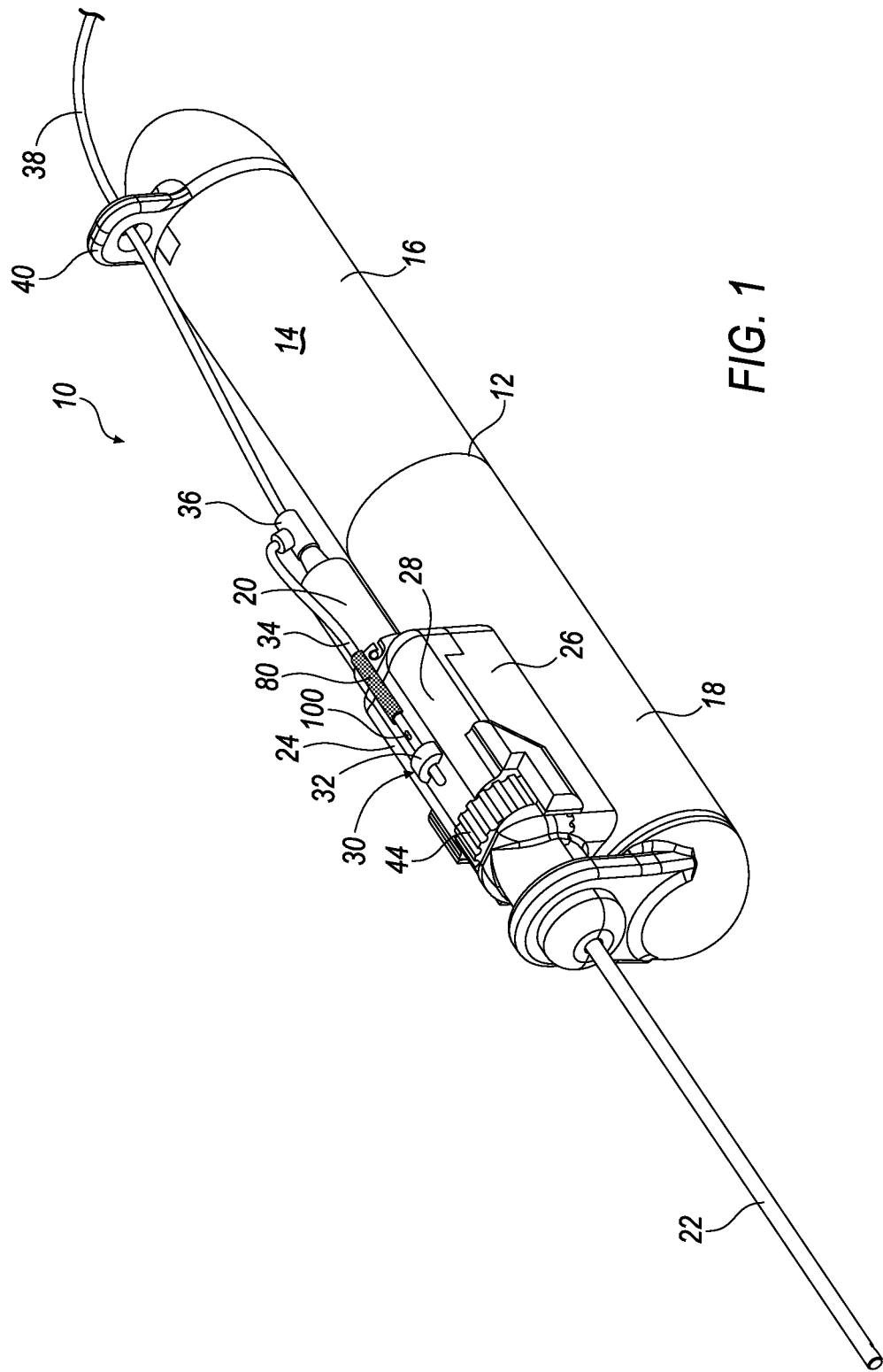
FIG. 1 is a perspective view of an exemplary tissue cutting device.
Figure 2:
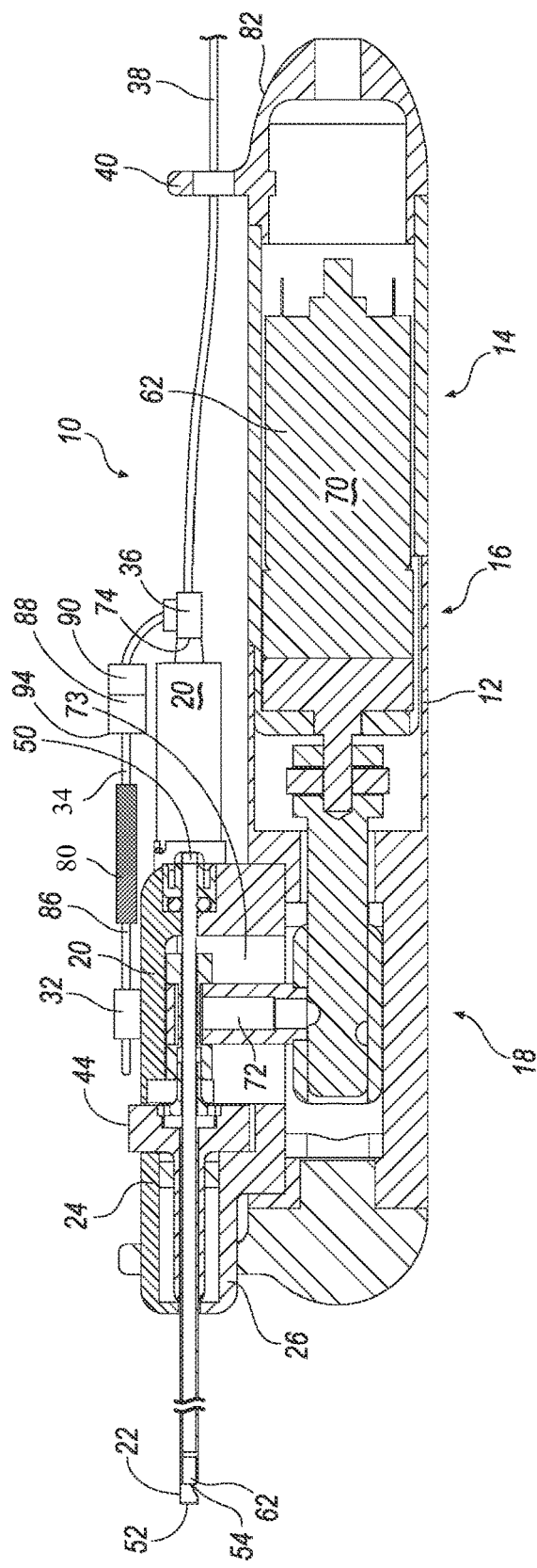
FIG. 2 is a cross-sectional view of the tissue cutting device of FIG. 1.

Referring to FIGS. 1 and 2, an exemplary tissue cutting device 10 includes a handpiece 12, an inner cannula 56 (best seen in FIGS. 3 and 4) and an outer cannula 22. In one exemplary embodiment, the handpiece 12 may be configured to be generally cylindrical in shape as well as sized and shaped to be grasped with a signal hand. The handpiece 12 includes a lower housing 14 which comprises a proximal section 16 and a distal section 18. A tissue collector 20 may be operatively connected to the upper housing 24. While shown attached directly to the upper housing 24, it is understood that the tissue collector 20 may be positioned remote from the upper housing 24. (See, e.g., FIG. 9.) The upper housing 24 may include a lower shell 26 and an upper shell 28 disposed above the lower shell 26. An aspiration control device 30 may be configured to control the level of vacuum within an inner cannula 56 of the tissue cutting device 10. The aspiration control device 30 may include a retainer 32 disposed on the upper shell 28 of the upper housing 24 that is configured to hold an aspiration device conduit 34. The retainer 32 may be secured by an adhesive or other manner. The aspiration device conduit 34 may be connected at a coupling 36 to the vacuum system hose 38. A hose connector 40 may also be provided. Hose connector 40 may provide a mechanism for securing a vacuum system hose 38 to the handpiece 12 to prevent accidental dislodgement of the vacuum system hose 38 during operation. A rotational dial 44 for rotating the outer cannula 22 with respect to the handpiece 12 may also be mounted to the upper housing 24.

Figure 3:
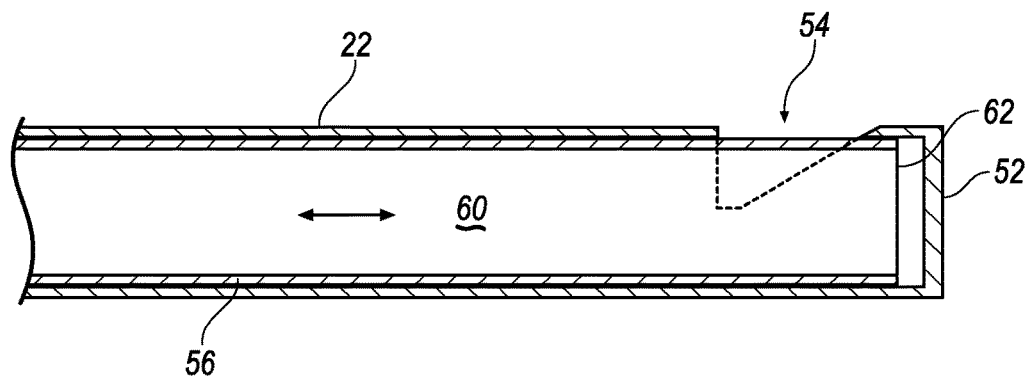
FIG. 3 is a partial cross-sectional view of a distal region of the outer cannula and inner cannula of the tissue cutting device of FIG. 1, depicting the inner cannula in a first relative position with respect to the outer cannula.
Figure 4:
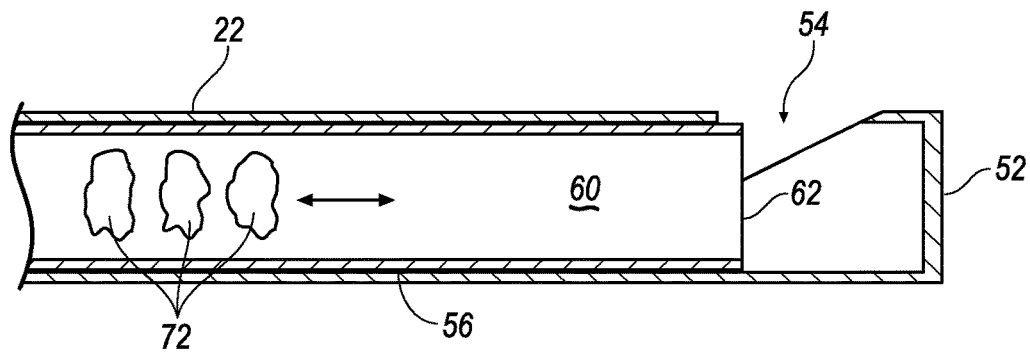
FIG. 4 is a partial cross-sectional view of a distal region of the outer cannula and inner cannula of the tissue cutting device of FIG. 1, depicting the inner cannula in a second relative position with respect to the outer cannula.

As best seen in FIGS. 3 and 4, the outer cannula 22 includes an open proximal end (not shown), a closed distal end 52, and a tissue receiving opening 54. As discussed above, the tissue cutting device 10 further includes the inner cannula 56, which is partially disposed in an outer cannula lumen 58. The inner cannula 56 is configured to reciprocate within the outer cannula lumen 58 and to cut tissue samples 72 entering the outer cannula 22 via the outer cannula tissue receiving opening 54. The inner cannula 56 reciprocates between a distal position, which is depicted in FIG. 3, and a proximal position, which is depicted in FIG. 4. The distal end 62 may be configured to cut tissue, as described herein. Inner cannula distal end 62 may also be beveled in a radially inward direction to create a sharp circular tip and facilitate tissue cutting. A motor 70 (shown in FIG. 2) may be disposed in the lower housing 14 of the handpiece 12 and be operably connected to the inner cannula 56 to drive the reciprocation of the inner cannula 56 within the outer cannula lumen 58. The motor 70 may be a reciprocating or rotary motor. In addition, it may be electric or hydraulic. The outer cannula 22 and the inner cannula 56 may be made of materials that are generally rigid, such as rigid plastics or metal. In one example, both cannulae are constructed of stainless steel, such as 304SS typically used in medical grade instruments.

In operation of the tissue cutting device 10, as the inner cannula 56 translates in the distal direction, it contacts tissue received in the tissue receiving opening 54 and the received tissue is severed and aspirated in the proximal direction along the inner cannula lumen 60 and received in the tissue collector 20. Thus, the inner cannula lumen 60 provides an aspiration path from the inner cannula distal end 62 to the inner cannula proximal end 64.

The tissue receiving opening 54 may have a number of shapes. In certain examples, when the tissue receiving opening 54 is viewed in plan, it has a shape that is generally square, rectangular, trapezoidal, ovular, or in the shape of the letter "D". In certain other exemplary implementations, the tissue receiving opening 54 is configured to direct tissue that it may be compressed as the inner cannula 56 translates in the distal direction.

Figure 9:
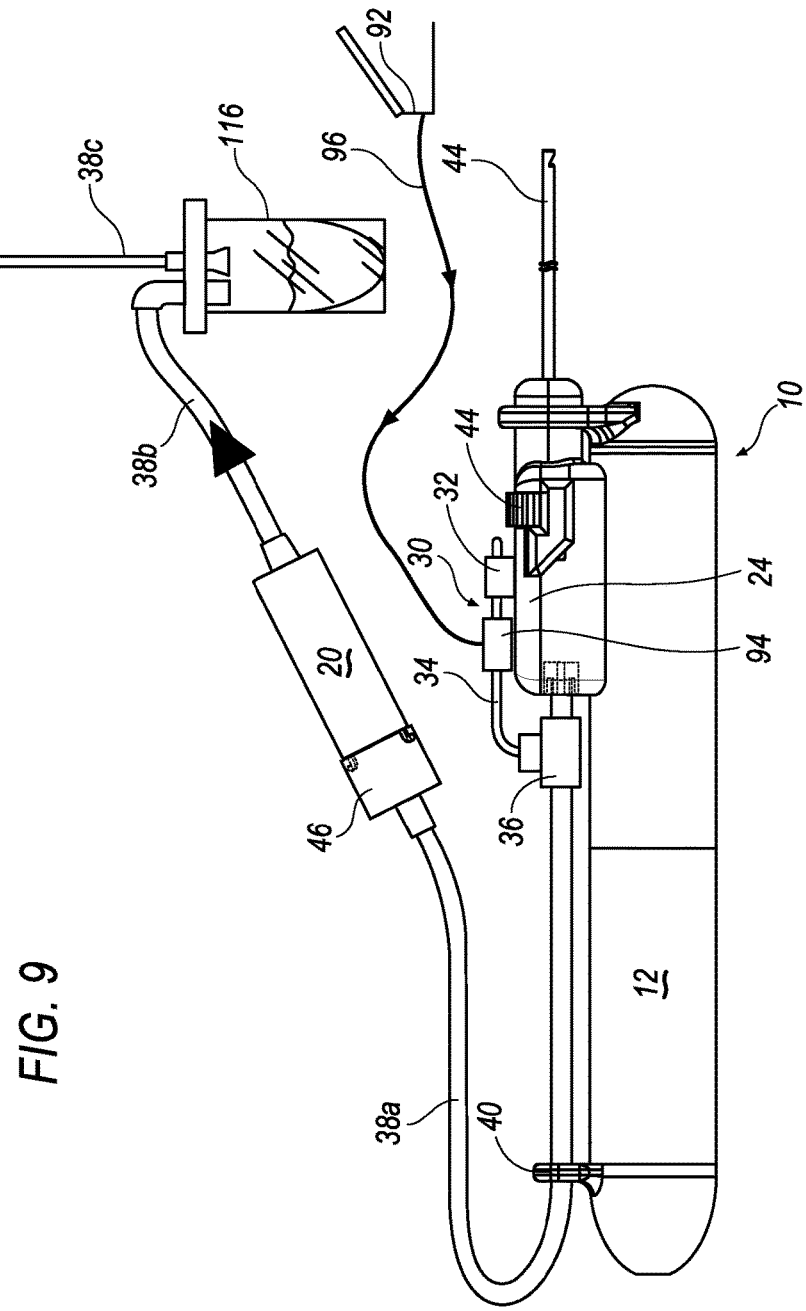
FIG. 9 is a tissue cutting system employing an exemplary aspiration cutting device for an aspiration control device.

As discussed above, the tissue collector 20 may be located remotely from the handpiece 12 and outside the sterile field during a tissue cutting operation (See FIG. 9.) Alternatively, as shown in FIGS. 1 and 3, tissue collector 20 may be removably connected to the handpiece 12. The tissue collector 20 may be connected to the upper housing 24 proximally of the inner cannula 56 to receive the aspirated tissue samples 72. In an exemplary arrangement, the tissue collector 20 may be generally cylindrical and hollow and have an interior valve that is in fluid communication with the inner cannula lumen 60 and a source of a vacuum, such as the vacuum system hose 38, is operably connected to the tissue collector 20 to direct samples into the tissue collector 20. The tissue collector 20 may be removably secured from the tissue cutting device. For example, in the exemplary arrangement shown, the tissue collector 20 may be removably secured to the upper housing 24 to allow for the periodic removal of collected tissue samples 72. It may be sealed to the upper housing 24 in a manner that provides a substantially leak-proof vacuum seal to maintain consistent aspiration of several tissue samples 72. The tissue collector 20 may also include a cylindrical cap 46 having a hollow interior for receiving a portion of the tissue collector 20 (as seen in FIG. 9.) The cap 46 may be fluidly connected to the vacuum system hose 38 and permit the tissue collector 20 to be removably attached to the hose 38 at the cap 46. A vacuum hose fitting 74 may be formed on the proximal end of the tissue collector 20 and be in fluid communication with the interior of the tissue collector 20 and with the vacuum system hose 38.

Figure 5:
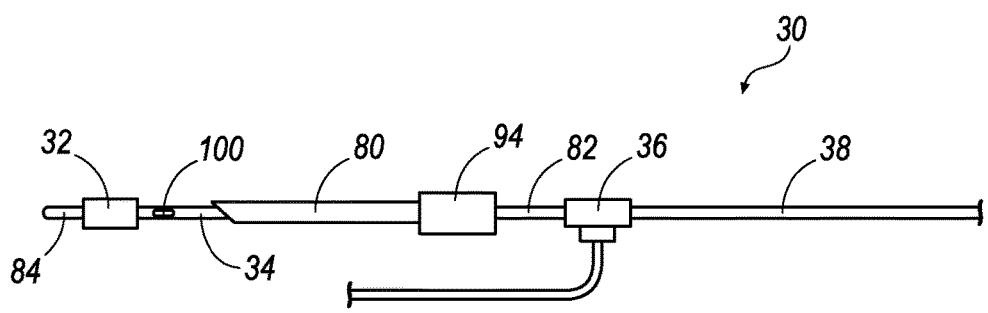
FIG. 5 is a perspective view of an exemplary aspiration control device of the tissue cutting device of FIG. 1.

Referring to FIGS. 5 and 6, aspiration control device 30 is described in further detail. Aspiration control device 30 may include an optional retainer 32, control device conduit 34 and a sleeve 80. The conduit 34 may define a conduit lumen 86 and have a conduit proximal end 82 and a conduit distal end 84. Further, because the aspiration control device 30 may be an add-on mechanism for existing handpieces, the aspiration control device 30 may need to be operably attached thereto. The retainer 32 may be secure the conduit 34 of the control device 30 at the distal end 84 to the upper housing 24 (as shown in FIG. 1) via an adhesive or other manner to prevent the conduit 34 from being displaced relative to the handpiece 12. The proximal end 82 may be configured to be received by the coupling 36. The coupling 36 may form a three-way union between the vacuum system hose 38, the inner cannula 56 and the conduit lumen 86. The coupling 36 may form a T-like shape whereby the proximal end 82 (as best seen in FIG. 5) of the conduit 34 may be inserted into one of the three openings in the coupling 36.

The sleeve 80 may be disposed around at least a portion of the conduit 34. As shown in FIG. 5, the sleeve 80 may be disposed around the conduit 34 between the retainer 32 and the coupling 36. Alternatively, the sleeve 80 may be disposed between conduit distal end 84 and the retainer 32.

A control device motor 88 and a driver 90 (as best seen in FIG. 2) may be in communication with the sleeve 80 and be configured to control the movement of the sleeve 80 in response to a user input from a user interface 92, e.g., pedal. (See, e.g., FIG. 9.) The control device motor 88 and the driver 90 may be housed in a motor housing 94. The driver 90 may be used to convert the rotational motion of motor 88 into the translational motion of the sleeve 80. The control device motor 88 may be a reciprocating or rotatory motor operably connected to the sleeve 80 to drive the reciprocation of the sleeve 80 over the conduit 34, as indicated by line A in FIG. 6. In additional, the motor 88 may be electric or hydraulic. The motor 88 may also be a linear motor configured to move the sleeve 80 linearly about the conduit 34, as indicated by line B. A linear motor may move the sleeve 80 in distal and proximal directions along the conduit 34, allowing the sleeve 80 to cover, all, none or a portion of vent 100, to be discussed in greater detail below. In one exemplary arrangement, the motor 88 may be a brushed DC motor. As shown and described in more detail with respect to FIG. 9, the user interface 92 may be connected to the motor 88 and the driver 90 via an input line 96. The input line 96 may carry an electrical signal from the user interface 92 to a control 98 disposed at and in communication with the motor 88.

As explained, the conduit 34 includes an aspiration vent 100. The sleeve 80 surrounds at least a portion of the conduit 34 and includes a sleeve body 106 and a sleeve tip 108. The sleeve tip 108 may be formed of a variety of shapes, as shown by way of example in FIG. 8. The vent 100 may also be defined by a variety of shapes, as shown by way of example in FIGS. 7A-D. As the sleeve 80 moves with respect to the conduit 34, so does the location of the sleeve tip 108 with respect to the vent 100. For example, as shown in FIG. 6, the sleeve tip 108 may cover a portion of the vent 100.

The coupling 36 facilitates a vacuum supply of vacuum to each of the conduit lumen 36 and the inner cannula lumen 60. In other words, the vacuum supplied by the vacuum system hose 38 is split between the two lumens via the coupling 36. When the vent 100 is uncovered, the supplied vacuum may be vented from the conduit 34 through the vent 100. Alternatively, when the vent 100 is closed by the sleeve tip 108, none of the supplied vacuum may be vented. Thus, as the vent 100 is closed, the level of vacuum supplied to the inner cannula lumen 60 is at its full level. That is to say, the vacuum previously applied to the conduit lumen 36 is redirected to the inner cannula lumen 60.

Accordingly, by closing the vent 100 with the sleeve 80 so that the sleeve tip 108 covers the entire the vent 100, the supplied vacuum in the conduit lumen 36 is eliminated. By eliminating the vacuum within the conduit lumen 36, the entirety of the vacuum supply is forced on the inner cannula lumen 60. Alternatively, when the vent 100 is not covered by the sleeve 80, at least a portion of the vacuum is vented from the conduit lumen 36 via the vent 100. Thus, by increasing the amount of vacuum vented by the conduit lumen 36, the vacuum of the inner cannula lumen 60 is decreased. The vacuum in the conduit lumen 36 may be totally eliminated or totally enabled, as described above. The vacuum level may also be varied by exposing a portion of the vent 100, as shown in FIG. 6. The sleeve 80 may be moved via the driver 90 and control device motor 88. The sleeve tip 108 may have a plurality of predefined positions, such that, depending on the user input at the user interface 92, a pre-established vacuum supply may be administered to the inner cannula lumen 60.

More specifically, the user's actuation and change in the position of the user interface 92 is defined by the user's observation of the tissue's response to the current aspiration level of the vacuum supply and the user's desired outcome and effect on the tissue and surrounding structures. For example, in certain situations, the user may desire to reduce the aspiration level of the vacuum supply to hold and move tissue away from critical structures, rather than having the aspiration level of the vacuum supply pull tissue within the tissue cutting device 10 and sever tissue samples.

Indeed, by implementing the system above, a repeatable and variable level of vacuum may be supplied to the inner cannula lumen 60 based on the position of the sleeve tip 108 relative to the vent 100. Thus, a user may apply a different level of vacuum at various times of a procedure. For example, some surgical procedures require the removal of unwanted tissues from critical structures such as neurovascular structures and brain tissue. It is important that the user have absolute control over the level of vacuum applied to various areas affected by the procedure at the tissue receiving opening 54 or tip. If an unwanted mass is being removed during the surgical procedure, a high level of vacuum may be required to remove the mass. Additionally or alternatively, a lower level of vacuum be appropriate when suctioning portions of the mass that are in close proximity to critical structures, such as brain mass or other nervous system tissues.

FIGS. 7A-D show a plurality of alternative vent 100 configurations. The vent 100 may be formed of a rectangular shape, as shown in FIG. 6. Alternatively, the vent 100 may be formed of an oblong or oval shape, a triangular shape, or any other shape that could be covered by the sleeve tip 108. FIGS. 8A-C show a plurality of alternative sleeve tip 108 configurations. For example, the sleeve tip 108 may include an angled tip 108, as shown in FIG. 6. Alternatively, the sleeve tip 108 may include a triangular tip 108, rectangular tip 108, or any other shaped tip 108 capable of covering the vent 100, in a known and predictable manner.

FIG. 9 is an exemplary implementation of a tissue cutting system configured to supply variable levels of vacuum to the inner cannula lumen 60. For example, the system may include cutting device 10, tissue collector 20, vacuum system hose 38, vacuum source 114, control device motor 88 and control 98. As discussed above, the tissue collector 20 may be located remotely from the handpiece 12 and may be placed far enough from the handpiece 12 to remain outside of the sterile field during a tissue cutting operation. The vacuum system hose 38a connects cap 46 of the tissue collector 20 to the coupling 36. A fluid canister 116 may be connected to the tissue collector 20 via the system hose 38b and to the vacuum source 114 via the system hose 38c. Thus, vacuum source 114 is in fluid communication with the tissue collector 20 and the inner cannula lumen 60, thereby generating a vacuum at the proximal end of inner cannula 64 to aspirate severed tissue samples 72 from the inner cannula distal end 62 to the tissue collector 20. Via the coupling 36, the vacuum source 114 is also in fluid communication with the conduit lumen 36 of aspiration control device 30. The level of vacuum applied to the inner cannula lumen 60 is variable and selectively controlled by the user via the user interface 92. Vacuum levels from about 0 to 29 in. Hg. may be applied, with a vacuum level of about 29 in. Hg. being most preferred. Lower levels of vacuum may be desired around critical structures, e.g., as the user moves into the critical zone of a micro-dissection phase of a cytoreduction operation. Higher aspiration levels are desirable as the user is in a gross debulking phase of the cytoreduction operation.

The sleeve 80 provides a mechanism for continuously adjusting and controlling the level of vacuum applied to the inner cannula lumen 60 based on a user's individual need, regardless of the vacuum level available from the vacuum source. The control 98 may receive and provide signals to the various components of the aspiration control device 30. It may provide signals to motor 88 and the sleeve 80 via an input line 96 extending from the control 98 to the sleeve 80. These signals are used to control the rotation or linear movement of the sleeve 80 in response to a desired level of vacuum. The control 98 receives signals from the user interface 92 via the input line 96. Thus, the control 98 provides immediate feedback to the motor 88 and the driver 90 which can in turn provide signals to the sleeve 80.

The user may adjust the level of vacuum by varying settings, or controls on the user interface 92. In one example, the user interface 92 is a pedal, specifically a foot pedal. In one example, the foot pedal may be depressed and configured to activate the control device motor 88. In exchange, the sleeve 80 may be rotated to a predetermined position depending on the amount of depression of the pedal. As pedal is depressed, the sleeve 80 is moved to apply a minimum level to a maximum level of vacuum. Foot pedal may provide continuous movement between fully open and fully depressed positions which in turn correspond to a plurality of vacuum levels that may be supplied to the inner cannula lumen 60. The user may also select from a plurality of intermediate positions available between fully open and fully depressed. These positions may correspond to a level of vacuum somewhere between the minimum level and maximum level.

The user interface 92, e.g., pedal, may be connected to control 98 via an electrical input. The control 98 may be electrically connected to the motor 88 and the motor 98 may be in communication with the sleeve 80. A vacuum sensor (not shown), which may be a temperature compensated solid-state pressure sensor, may be positioned within the inner cannula lumen 60. Alternatively, the vacuum sensor may be placed in the system hose between the inner cannula 56 and the coupling 36. The sensor may be electrically connected to the control 98.

Figure 10:
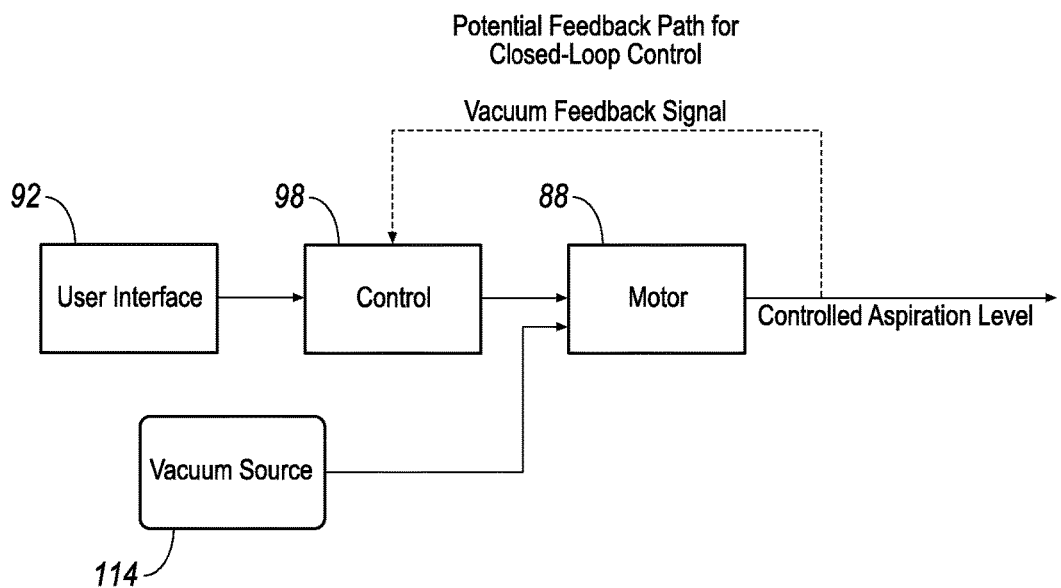
FIG. 10 is an exemplary control system for the exemplary aspiration control device.

FIG. 10 presents an exemplary closed loop control path for automatic control of the vacuum level of the inner cannula lumen 60. In operation, the control 98 is responsive to the input signal provided by the user interface 92 over the input line 96. The control 98 therefor facilitates a desired level of vacuum to the inner cannula lumen 60 in response to input at the user interface 92. The actual vacuum level provided to the inner cannula lumen 60 is sensed by a vacuum sensor, which provides a feedback signal to the vacuum feedback input. The control 98 is then operable to compare the vacuum feedback signal with the vacuum command signal and correspondingly adjust the position of the sleeve 80 to achieve the desired vacuum level within the inner cannula lumen 60. More specifically, a linear actuator or rotary actuator that is electronically or pneumatically/fluidically controlled may be operatively connected to the sleeve 80 to move the sleeve appropriately as needed for the desired vacuum level. The sleeve 80 could be actively actuated in both a forward and rearward direction. In yet another embodiment, the actuator may be configured to be spring biased so that active actuation would only be directed in a single direction, against the biasing force of the spring.

In another example, the control 98 may be replaced by individual microprocessors controlling the input and output for controlling the operation of the control device motor 88. These microprocessors may be PIC16CXX Series microcontrollers provided by Microship, Inc. of Chandler, Ariz. The microcontroller can provide output to the control 98 and have its own display, such as an LED display, indicative of tis operational status.

In certain examples, the user may adjust the level of vacuum to achieve a desired level of "traction" in the tissue surrounding the tissue to be severed. Traction may refer to the exertion of a pulling force on tissue surrounding the target tissue to be severed. In some instances, traction may be visualizable by the surgeon with the use of a magnification instrument, such as a microscope or an endoscope. The level of vacuum will also determine the amount of unsevered tissue that is drawn into the tissue receiving opening 54, and therefore, the size of the severed tissue snippets. Therefore, when fine shaving operations re desired, the vacuum level will be relatively lower level than if debulking (large scale tissue removal) is performed. Of course, the pre-selected maximum vacuum level will also affect the maximum size of tissue that is drawn into the tissue receiving opening 54, and therefore, will affect the maximum size of severed tissue samples 72 during any one operation. Also, the vacuum level may be adjusted based on the elasticity, fibrotic content, and hardness/softness of the tissue. As explained, the variable vacuum level may be achieved by altering the coverage of the vent 100 by the sleeve 80. Thus, in operation, the larger the desired tissue sample, the more coverage of the vent 100 by the sleeve 80, creating a higher level of vacuum.

In another example, the user interface 92 may be a knob used to set a preselected vacuum level. The knob may then activate the device motor 88, which may in turn rotate the sleeve 80 to an appropriate position relative to the selected vacuum level. A control console may also be used that includes an analog or digital display. The display may indicate the selected vacuum level.

In the foot pedal example, a user may not need to manually adjust a knob or control interface with his or her hands, allowing for more control and accuracy in guiding the cutting device. Instead, a user may depress the foot pedal with his or her foot and generates an appropriate vacuum level. Control interface may be used in conjunction with the pedal and provide a display of the current vacuum level. Thus, a user could adjust the level of vacuum by depressing or lifting the foot pedal in response to the level displayed via the control console.

As explained, the tissue cutting device 10 may be used to perform a cutting operation. However, the tissue cutting device 10 may also be used as an aspiration wand without cutting any tissue, thus operating as a multi-functional surgical device. The tissue cutting device 10 may also be used as a blunt dissector whereby the outer cannula 22 may be used to move or manipulate tissue to position tissue for cutting. More specifically, when used for tissue manipulation, the outer cannula 22 may be manipulated to allow a user to scrape tissue from a structure, such as critical vessels, thereby minimizing or even preventing any damage to such structures. In one exemplary procedure, the tissue cutting device 10 may be deactivated such that inner cannula 64 stops moving. In this configuration, the vent 100 on the outer cannula 22 may be used as a rake to pull across tissue and rake tissue off critical structures and/or vessels. Additionally, the user may vary the aggressiveness of this action by the lack of vacuum being delivered to the vent 100 or by varying the amount of vacuum being delivered to the vent 100, as well as the amount of downward force applied to the subject tissues.

In one exemplary configuration, the inner cannula 56 may be deactivated such that a distal end of inner cannula 56 is positioned proximally of the tissue receiving opening 54, allowing a user determined level of vacuum may be supplied to the tissue receiving opening 54. As explained, vacuum may be used to pull tissue away from critical structures such that the vacuum supply is used as the retraction mechanism or the tissue holding mechanism in the same way that the introduction of a separate suction cannula device would be used. Thus, in moving tissue away from critical structure, a lower level of vacuum may be necessary than that required to remove a large mass. Moreover, as the procedure is performed, the user may wish to easily adjust the level of vacuum. For example, initially the user may be removing a large mass. However, as the mass is removed, the tissue receiving opening 54 may become closer and closer to critical structures. As this happens, the user may gradually decrease the level of vacuum to more accurately and carefully remove tissue in abutting the critical structure.

In another exemplary use, the outer cannula 22 may be used as a vessel tapenade. In this application, the outer cannula 22 may be selectively pressed on a vessel to assist in providing direct pressure on the offending vessel to control and stop bleeding, as the outer cannula 22 does not generate heat. In yet another use, vacuum may be simultaneously applied to the vent 100 to evacuate the field of the surgical site prior and/or during the use as a tapenade so that the user may be able to visualize and determine the exact location of the offending vessel that requires hemostasis. Furthermore, since the vent 100 is configured on the side of the outer cannula 22, the distal end of the outer cannula 22 or the non-the vent 100 side of the outer cannula 22 may be used as the tapenade, for example.

In another example, vacuum may be used to aspirate fluid from a surgical site to clear the field and in conjunction with the tissue cutting device 10 when activated to resect and remove target tissue from the surgical site. Because the tissue cutting device 10 may be used in a variety of manners, the tissue cutting device 10 also allows flexibility for a user to vary his or her approach to each surgical situation. By using a foot pedal as the user interface 92, a user may change the vacuum level without use of the user's hands.

Figure 11:
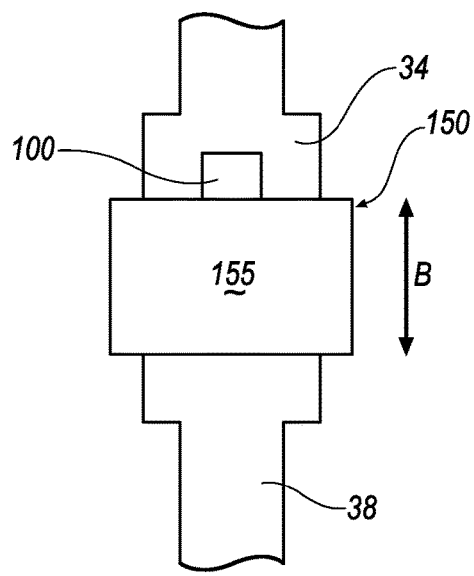
FIG. 11 is a partial top plan view of a portion of another exemplary aspiration control device.

FIG. 11 is a partial top plan view of a portion of another exemplary aspiration control device. Similar to the example shown in FIG. 6, a conduit 34 may define a conduit lumen (not shown in FIG. 11) and a vent 100. A sleeve 155 may surround at least a portion of the conduit 34 and may be configured to selectively cover at least a portion of the vent 100 in response to user input at the user interface 92, similar to sleeve 80 as shown in FIG. 6. The sleeve 155 may be included as part of a sleeve device 150. Moreover, the sleeve 150 may define any of the tip configurations shown in FIGS. 8A-8C and the vent 100 may include any of the configurations shown in FIGS. 7A-7D.

The sleeve device 150 may include a control device motor 88 and driver 90 (not shown in FIG. 11) configured to control the movement of the sleeve 155 in response to the user input. The sleeve 155 may be a bobbin-like mechanism configured to move linearly about the conduit 34, as indicated by line B. The sleeve device 150 may house the device motor 88 and driver 90. Additionally or alternatively, the motor 88 and driver 90 may be housed in a separate housing (not shown in FIG. 11). As explained, the control device motor 88 may be a linear motor or actuator, a ball and screw drive, coil and permanent magnet arrangement, etc. configured to move the sleeve 80 linearly about the conduit 34, as indicated by line B. A linear motor, which is controlled by user interface 92, may move the sleeve 80 in distal and proximal directions along the conduit 34, allowing the sleeve 80 to cover, all, none or a portion of vent 100. The control device 30 may be connected either directly or indirectly to the vacuum source 114 via the hose 38c to provide controlled suction to surgical instrument 10.

Figure 12:
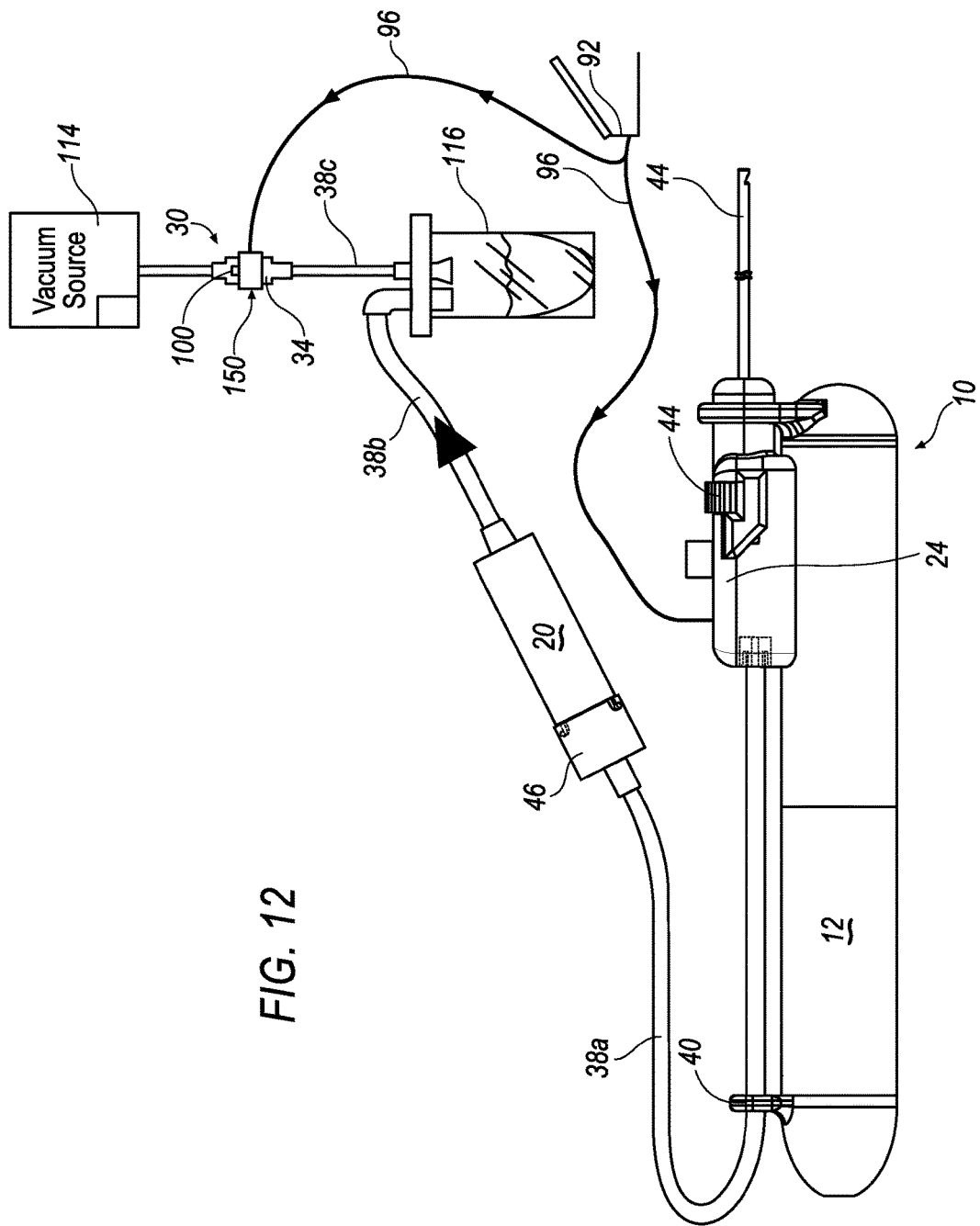
FIG. 12 is an exemplary tissue cutting system employing the exemplary aspiration cutting device of FIG. 11 at a first location within the tissue cutting system.
Figure 13:
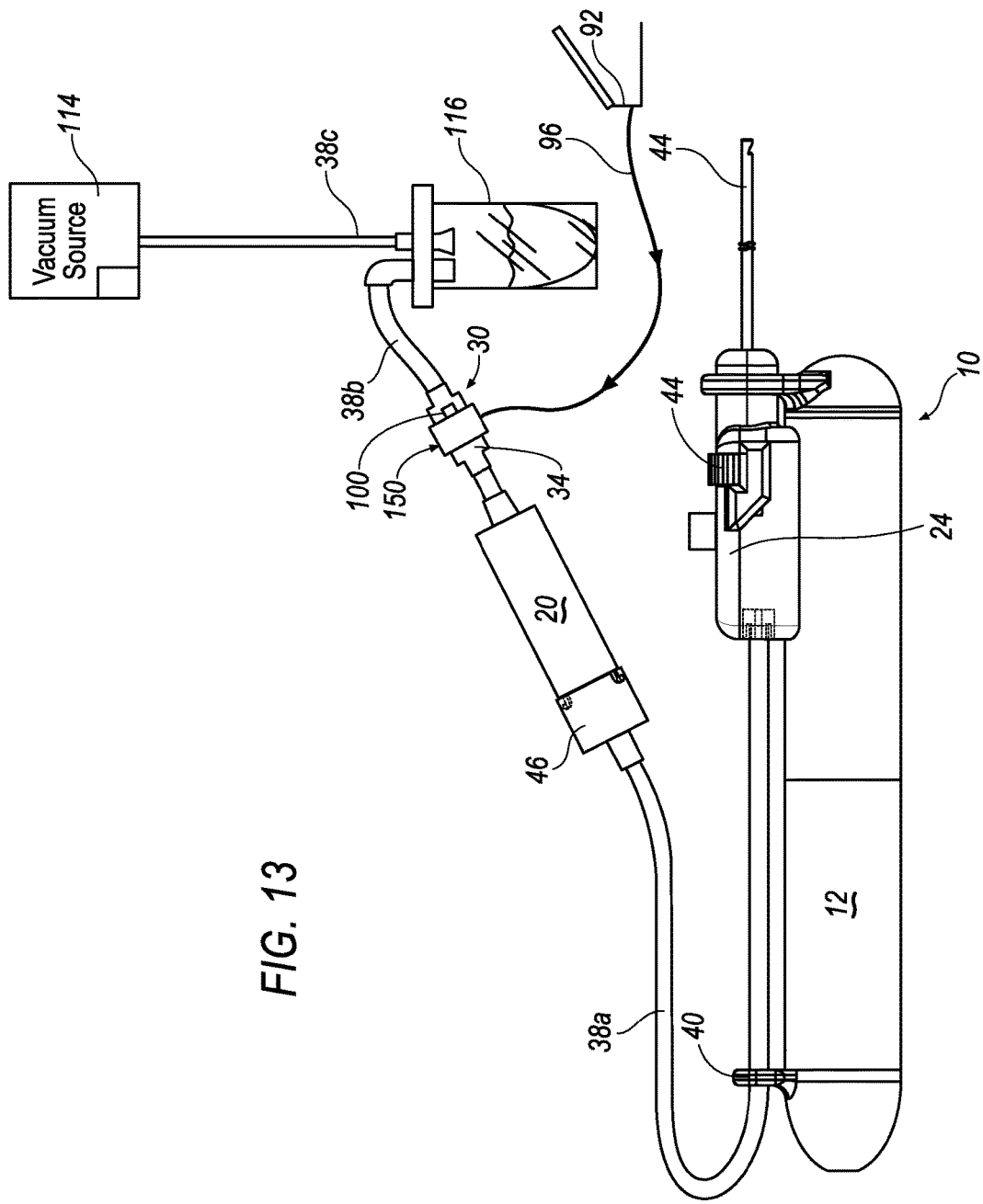
FIG. 13 is an exemplary tissue cutting system employing the exemplary aspiration cutting device of FIG. 11 at another location within the tissue cutting system.
Figure 14:
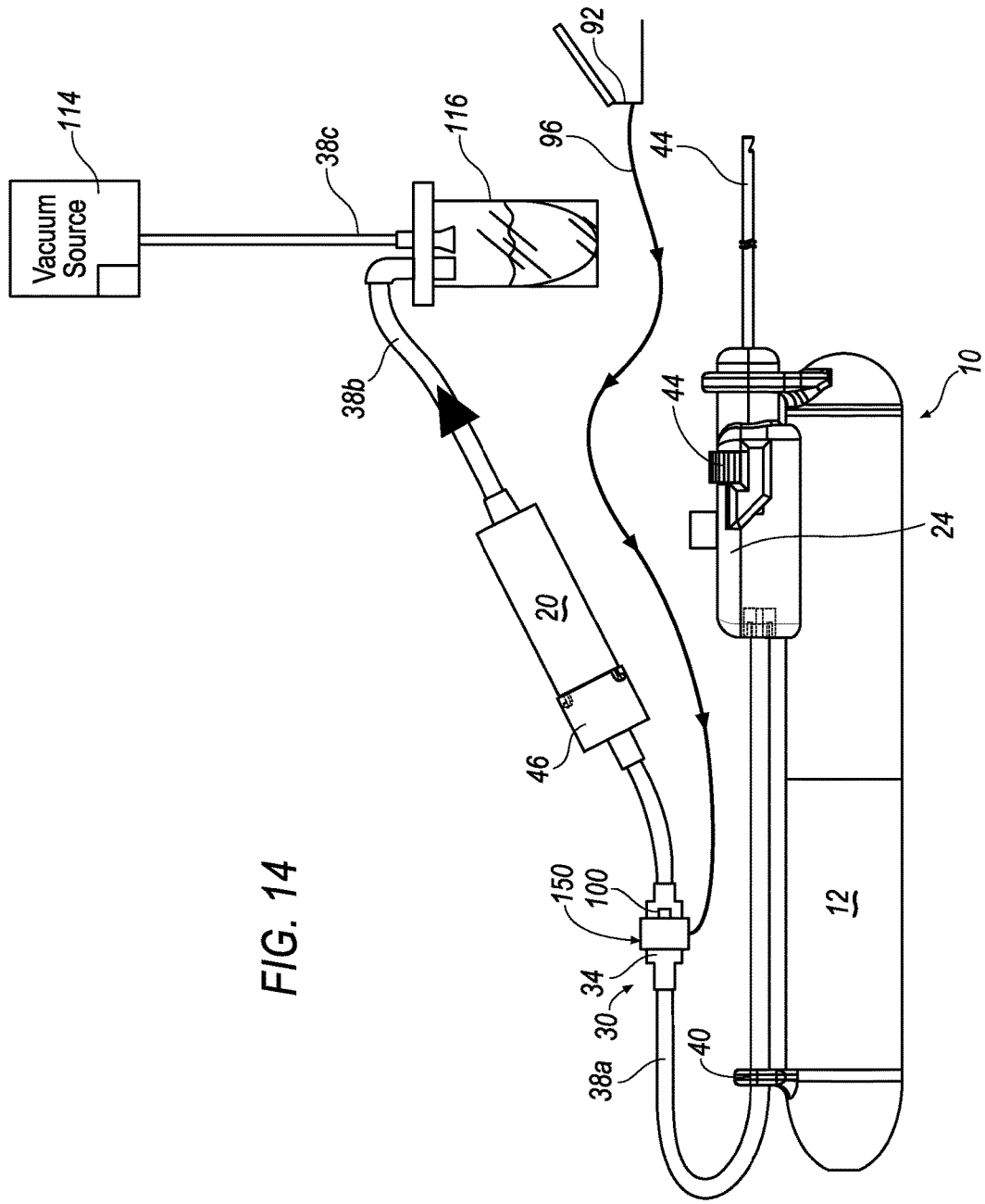
FIG. 14 is an exemplary tissue cutting system employing the exemplary aspiration cutting device of FIG. 11 at another location within the tissue cutting system.
Figure 15:
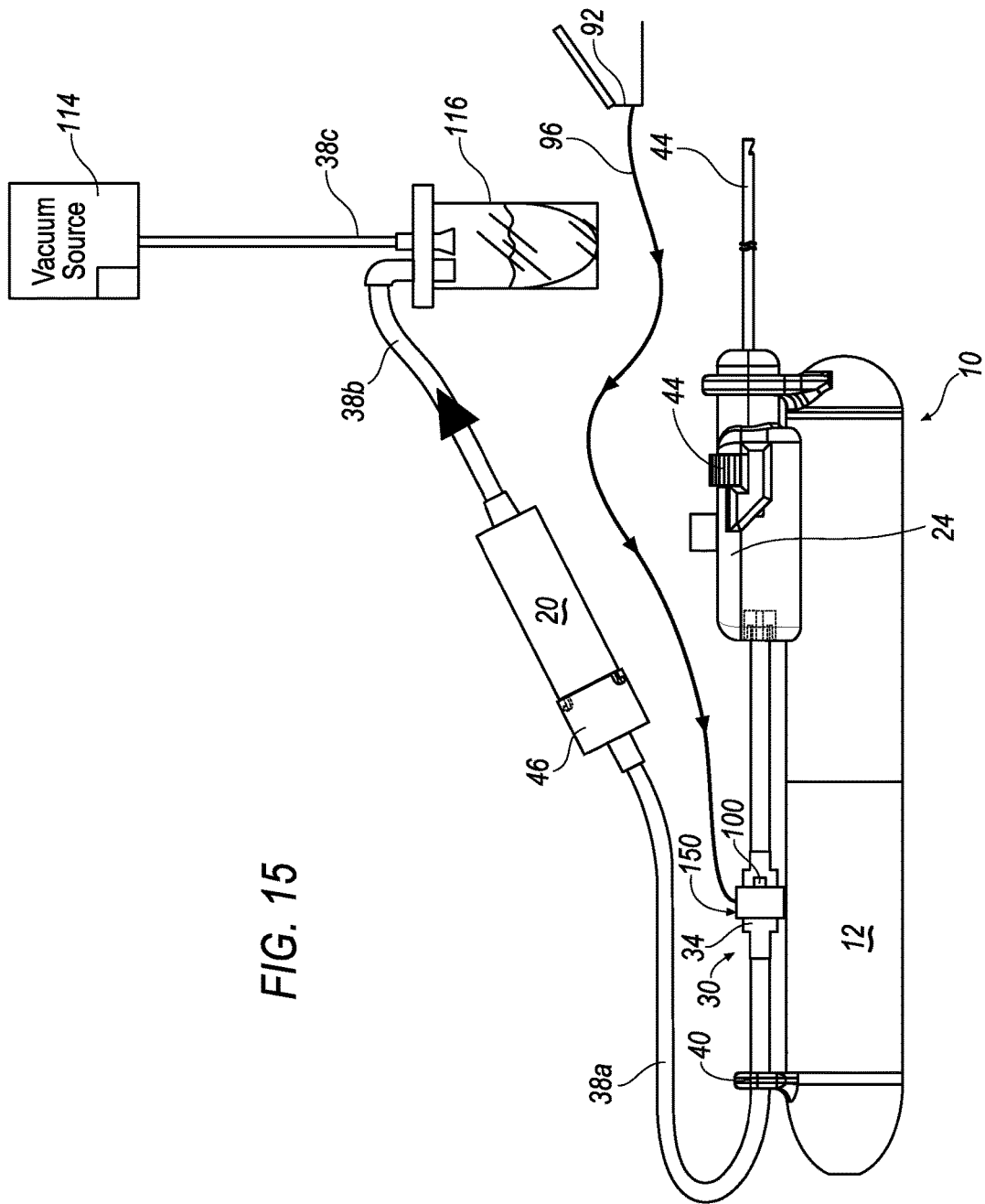
FIG. 15 is an exemplary tissue cutting system employing the exemplary aspiration cutting device of FIG. 11 at another location within the tissue cutting system.

FIGS. 12-16 are exemplary surgical instruments employing the exemplary aspiration control device 30 of FIG. 11. The aspiration control device 30 may be arranged at various locations along the vacuum system line 38. FIG. 12 illustrates an example where the control device 30 is arranged between the vacuum source 114 and the fluid canister 116 within system hose 38c. FIG. 13 illustrates an example where the control device 30 is arranged between the fluid canister 116 and the tissue collector 20 on system hose 38b. FIG. 14 illustrates an example where the control device 30 is arranged between the tissue collector 20 and the hose connector 40 on system hose 38a. FIG. 15 illustrates an example where the control device 30 is arranged between the hose connector 40 and the upper housing 24 of the handpiece 12. Although not shown, additional connectors, spacers and/or supports may be arranged along the hose 38 to provide additional support for the hose 38. For example, additional supports may be arranged along the handpiece and be configured to maintain the hose 38 along the handpiece during operation.

With respect to the example shown in FIG. 12 where the aspiration control device 30 is placed in line with system hose 38c, the aspiration control device 30 may be outside of the biological material pathway. That is, the control device 30 is not susceptible to biological contamination, which may permit the aspiration control 30 to be a reusable component. This may also be the case with respect to the example shown in FIG. 16. The examples show in FIGS. 13-15 may also be reusable. Moreover, the control device 30 may be disposable and may be used in conjunction with a reusable interface or pedal 92.

The control device 30, as explained, may act as a valve to affect the level of vacuum on the hose 38c by exposing various portions of the vent 100 with the sleeve 150. As the vent 100 is closed via the sleeve 150, the more suction from the vacuum source 114 is supplied to the hose 38c. Conversely, as the vent 100 is uncovered, the more suction from the vacuum source 114 is bleed through the vent, decreasing the suction supplied to the hose 38c.

Figure 16:
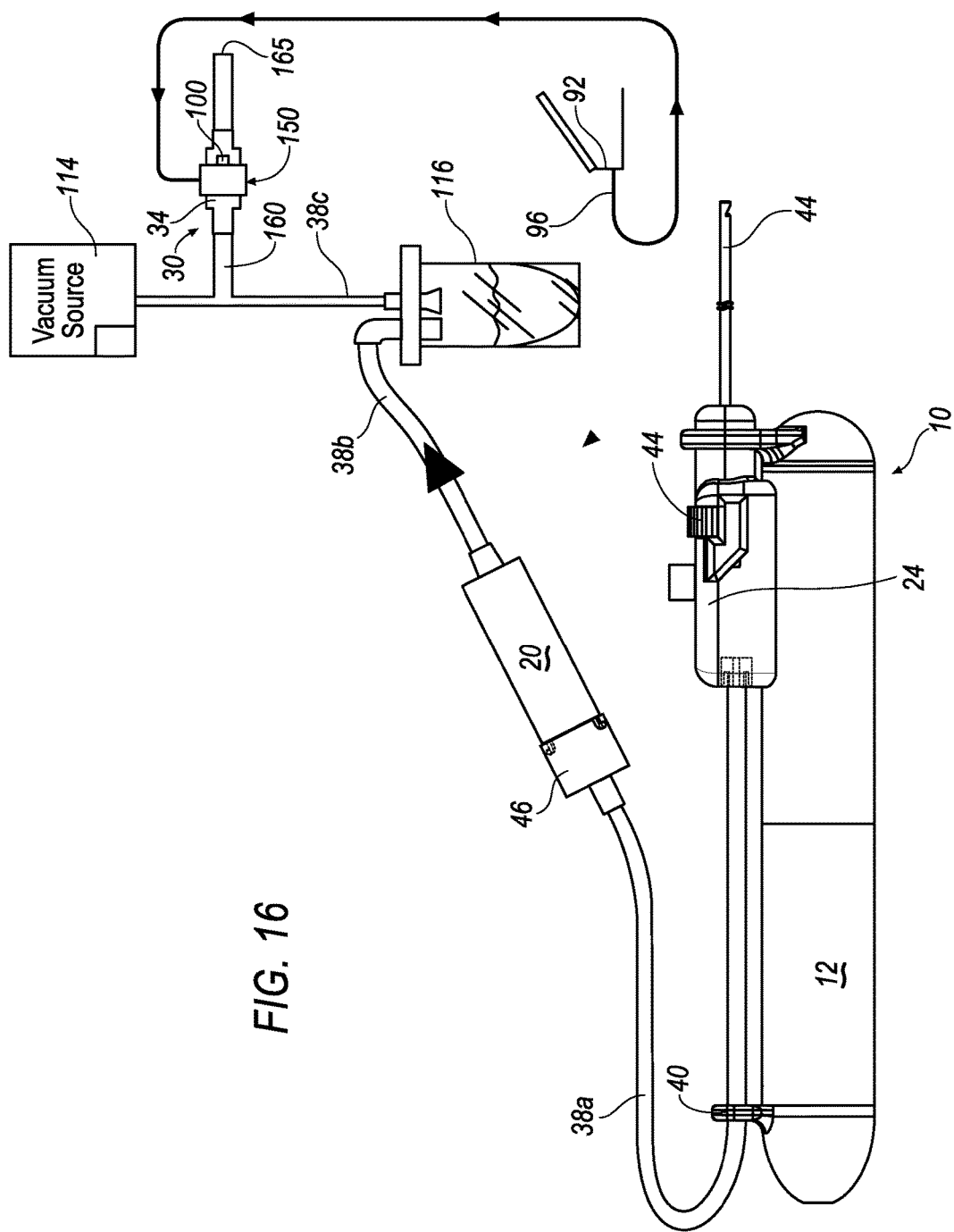
FIG. 16 is an exemplary tissue cutting system employing the exemplary aspiration cutting device of FIG. 11 at another location within the tissue cutting system.

FIG. 16 illustrates another arrangement of the control device 30 where the control device 30 may be arranged at the system host 38c. In this configuration, the control device 30 may be arranged on a separate tube 160 that forms a T-junction with the hose 38c. A distal end 165 of the tube may be closed. The control device 30 may, similar to the examples above, affect the level of vacuum on the hose 38c by exposing and closing the vent 100 in response to interaction at the interface 92. Moreover, although the arrangement is shown by way of example in FIG. 16 to be arranged at the system hose 38c, the control device 30 may also be arranged in a t-like arrangement anywhere along the aspiration pathway, including at any one of the other system hoses 38a and 38b.

As mentioned, the control device 30 may be arranged outside the sterile field during a tissue cutting operation. In addition to the device 30 being reusable, the device may also be used in connection with existing vacuum devices without modifying the vacuum device. That is, the control device 30 may be used with existing cutting devices and vacuum supplies as an add-on component without further modifications to those devices.

Accordingly, the aspiration control device may be arranged at various positions along the vacuum system hose and may be configured to control the pressure drop delivered to the surgical instrument in response to user input at the user interface.

It will be appreciated that the surgical device/tissue cutting devices and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A tissue cutting device, comprising:
    an aspiration control device arranged between a vacuum source and a fluid canister and having
        a conduit defining a conduit lumen and a vent that is open to the conduit lumen,
        a sleeve slidably disposed about the conduit, and
        a device motor in communication with the sleeve and configured to move the sleeve relative to the vent in response to an input signal from a user interface, wherein the position of the sleeve relative to the vent provides for a desired vacuum level within the conduit, wherein a predefined position of the sleeve corresponds to a predefined level of vacuum to be supplied to an inner cannula lumen.

2. The device according to claim 1, wherein the sleeve has a sleeve body and a sleeve tip extending from a distal end of the sleeve body, the tip being configured to cover at least a portion of the vent.

3. The device according to claim 2, wherein the motor is configured to drive the sleeve longitudinally along the conduit to place the sleeve tip in a predefined position relative to the vent.

4. The device of claim 1, wherein the predefined position of the sleeve corresponds to a depression position of the user interface.

5. The device of claim 1, further comprising a tube forming a T-junction with a vacuum hose between the vacuum source and tissue collector, wherein the conduit is arranged on the tube.

6. The device of claim 5, wherein the tube includes a closed distal end.

7. A tissue cutting device, comprising:
    an aspiration control device having a conduit defining a vent and a sleeve slidably disposed about the conduit and configured to move with respect to the vent,
    a device motor in communication with the sleeve and configured to move the sleeve relative to the vent in response to an input signal from a user interface, wherein a predefined position of the sleeve corresponds to a predefined level of vacuum to be supplied to an inner cannula lumen.

8. The device of claim 7, wherein the aspiration control device is arranged between a vacuum source and a fluid canister.

9. The device of claim 7, wherein the aspiration control device is arranged between a fluid canister and a tissue collector.

10. The device of claim 7, wherein the aspiration control device is arranged between a tissue collector and a handpiece of the tissue cutting device.

11. A tissue cutting device, comprising:
    an aspiration control device arranged between a vacuum source and a fluid canister and having
        a conduit defining a conduit lumen and a vent that is open to the conduit lumen,
        a sleeve slidably disposed about the conduit,
        a device motor in communication with the sleeve and configured to move the sleeve relative to the vent in response to an input signal from a user interface, wherein the position of the sleeve relative to the vent provides for a desired vacuum level within the conduit, and
        a tube forming a T-junction with a vacuum hose between the vacuum source and fluid canister, wherein the conduit is arranged on the tube.

* * * * *